United States Patent
Edvardsson

(12)
(10) Patent No.: US 7,149,578 B2
(45) Date of Patent: Dec. 12, 2006

(54) IMPLANTABLE MEDICAL DEVICE WITH SLOTTED HOUSING SERVING AS AN ANTENNA

(75) Inventor: Kurt Olov Edvardsson, Täby (SE)

(73) Assignee: St. Jude Medical AB, Jarfalla (SE)

( * ) Notice: Subject to any disclaimer, the term of this patent is extended or adjusted under 35 U.S.C. 154(b) by 341 days.

(21) Appl. No.: 10/682,954

(22) Filed: Oct. 10, 2003

(65) Prior Publication Data

US 2005/0004614 A1 Jan. 6, 2005

(30) Foreign Application Priority Data

Jul. 3, 2003 (SE) .................................... 0301980

(51) Int. Cl.
*A61N 1/372* (2006.01)
(52) U.S. Cl. ........................................................ 607/17
(58) Field of Classification Search .................. 607/17, 607/30, 32, 36–38, 60; 343/700 MS, 742
See application file for complete search history.

(56) References Cited

U.S. PATENT DOCUMENTS

| 4,243,042 A | 1/1981 | Ware |
| 4,443,218 A | 4/1984 | DeCant, Jr. et al. |
| 5,121,127 A * | 6/1992 | Toriyama ............. 343/700 MS |
| 5,602,556 A * | 2/1997 | Bowers ....................... 343/742 |
| 5,861,019 A | 1/1999 | Sun et al. |
| 5,873,840 A | 2/1999 | Neff |
| 5,913,881 A | 6/1999 | Benz et al. |
| 6,169,925 B1 * | 1/2001 | Villaseca et al. ............. 607/60 |
| 6,240,317 B1 * | 5/2001 | Villaseca et al. ............. 607/60 |
| 6,505,072 B1 | 1/2003 | Linder et al. |
| 6,561,975 B1 | 5/2003 | Pool et al. |
| 2002/0065539 A1 | 5/2002 | Von Arx et al. |
| 2002/0095195 A1 | 7/2002 | Mass |
| 2002/0123776 A1 | 9/2002 | Von Arx et al. |
| 2004/0215280 A1* | 10/2004 | Dublin et al. ................. 607/36 |

* cited by examiner

Primary Examiner—George Manuel
(74) Attorney, Agent, or Firm—Schiff Hardin LLP

(57) ABSTRACT

An implantable medical device has a conductive housing, electronic circuitry for the operation of the implantable medical device, and radio frequency circuitry for transmitting and/or receiving radio frequency signals, the electronic circuitry and the radio frequency circuitry being interconnected and arranged within in the housing. The housing has at least one slot therein, and a slot feed operatively interconnected between the radio frequency circuitry and the slot. The electrically conductive housing provided with the at least one slot is operable as an antenna for the radio frequency signals. The electric circuitry, the radio frequency circuitry, and the interconnection can be enclosed by the housing so that they are shielded from external radiation in any direction.

28 Claims, 4 Drawing Sheets

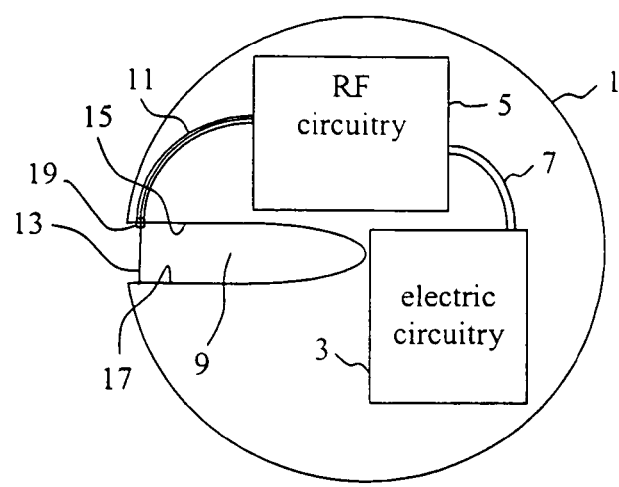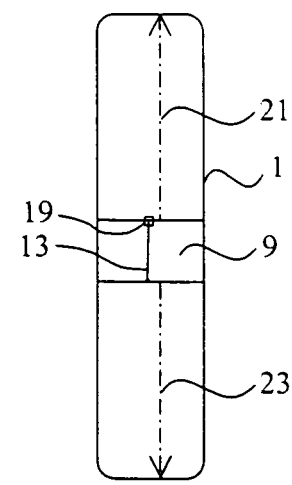
Fig. 1a
Fig. 1b
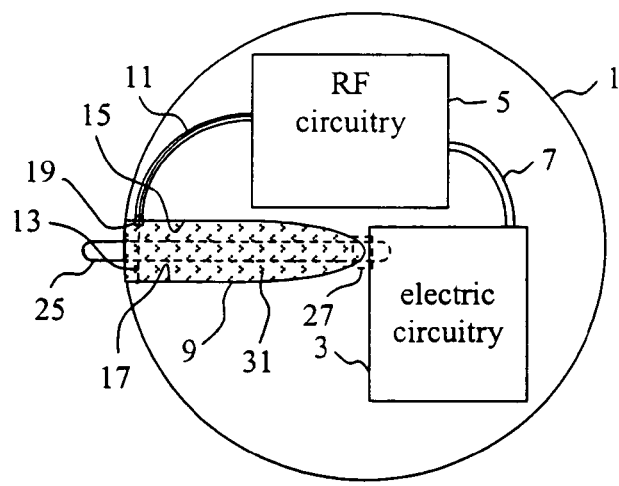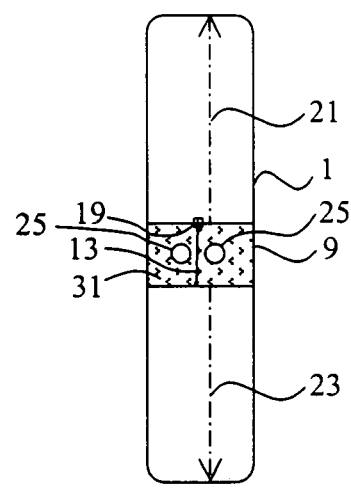
Fig. 2a
Fig. 2b

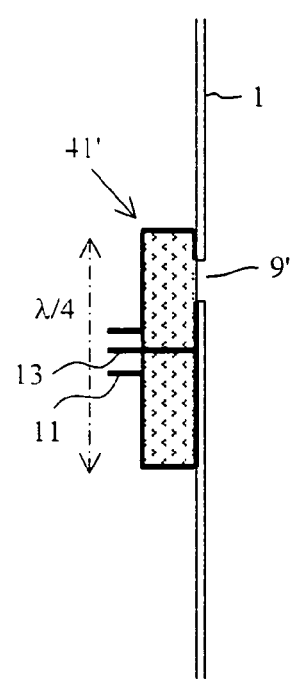
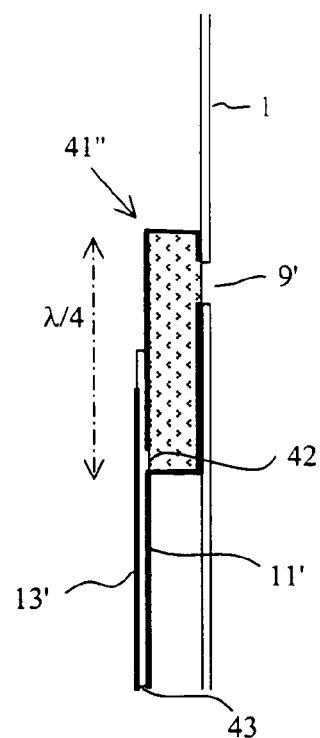
Fig. 6    Fig. 7
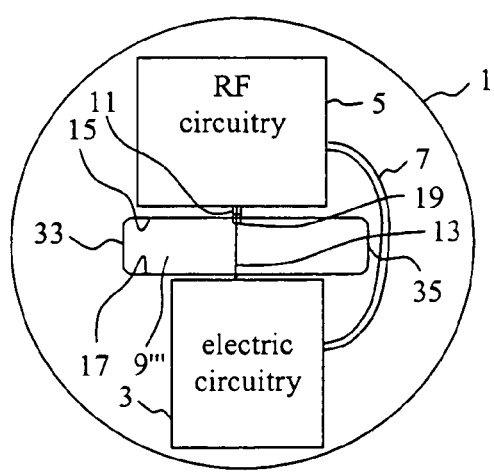
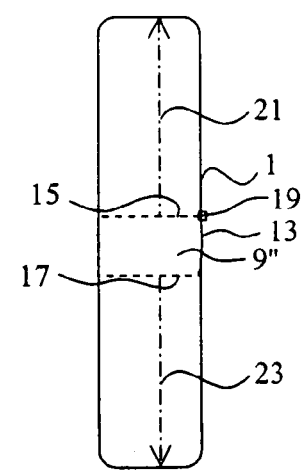
Fig. 8a    Fig. 8b

IMPLANTABLE MEDICAL DEVICE WITH SLOTTED HOUSING SERVING AS AN ANTENNA

BACKGROUND OF THE INVENTION

1. Field of the Invention

The present invention relates to an implantable medical device.

2. Description of the Prior Art

In an implantable medical device, such as a cardiac pacemaker, an implantable cardioverter/defibrillator, or an insulin dispenser, telemetry is used e.g. to change or modify operation characteristics of the implantable device or to read out data from the implantable medical device to monitor its functioning or to obtain information about the patient in whom the device is implanted. Telemetry systems for implantable medical devices have utilized radio-frequency energy to enable communication between the implantable device and an external programmer device.

Earlier telemetry systems used a rather low radio frequency, i.e. 13.5 MHz, as a carrier wavelength for communication between an antenna of the implantable device and an antenna of the external programmer device, which were inductively coupled to each other. Due to the very poor operating distance of this technique, the exterior antenna had to be located in close proximity to the implantable device, typically within a few inches. Further, the communication suffered from low transmission data rate.

Recently, telemetry systems using a radio frequency data link operating at a much higher frequency, around 400 MHz, have been proposed, which enable two improvements to be made. First, the antenna efficiency can be improved allowing the range between the pacemaker and the external antenna to be extended. Second, the transmission data rate can be improved. Even higher frequencies can be used such as those within the ISM-band at 2400–2485.5 MHz.

U.S. patent application Publication 2002/0095195 discloses an implantable medical device utilizing such far-field electromagnetic radiation to allow communication over a large distance. Two conductive halves of a housing for the implantable device act as a dipole antenna for radiating and receiving far-field radio frequency radiation modulated with telemetry data. The conductive halves are separated by an insulating header, in which conducting leads can be located.

Although U.S. patent application Publication 2002/0095195 discloses a manner to utilize the limited space for the antenna function, but, nevertheless, there are several limitations as to the use of an implantable medical device in which two separated conductive halves of the housing act as a dipole antenna.

First, because the header, made of dielectric material, is disposed between the two conductive halves, this allows external interfering radiation to enter the implantable device and interfere with signals transmitted within any of the two conductive halves or with signals transmitted across the dielectric header.

Second, in order to hermetically seal the two housing halves, a number of feed-throughs between them are needed since different electric circuitry is located in different housing halves to effectively use the available space.

Third, the design of the implantable medical device does not allow for an optimum location of the conducting leads with respect to possible interference of the therapy signals by radio frequency signals fed to or received by the dipole antenna. The antenna type lacks a voltage node on its surface, where the electric field has a minimum, so the therapy signals would not have been obvious to a person of ordinary skill in the would be affected to a minimum extent.

Finally, the mechanical structure of this known implantable medical device seems not to be optimum, because two housing portions of a conductive material have to produced, and must be fixed to and hermetically sealed against an intermediate piece of dielectric material. The manufacturing is further complicated by the need for a number of feed-throughs.

SUMMARY OF THE INVENTION

An object of the present invention is to provide an implantable medical device having an antenna that overcomes the above-mentioned problems.

It is a particular object of the invention to provide such an implantable medical device that exhibits an overall improved antenna performance in comparison to known implantable medical devices. Higher antenna efficiency implies increased usable range for an exterior antenna.

A further object of the invention is to provide such an implantable medical device that is shielded from external radio frequency radiation in any direction.

A still further object of the invention is to provide such an implantable medical device that has a minimum number of feed-throughs in the housing thereof.

A yet further object of the invention is to provide such an implantable medical device that has conducting leads extending from the implantable medical device, which allows conducting leads to be located so as to be affected as little as possible by radiation transmitted and/or received by the antenna of the implantable medical device.

A still further object of the invention is to provide such an implantable medical device, in which the antenna is easy to manufacture to a low cost, easy to tune, and wherein the antenna enables an efficient use of available space.

Another object of the invention is to provide such an implantable medical device that is reliable and particularly mechanically durable.

These objects, among others, are achieved in an implantable medical devices having an electrically conductive housing, in which electronic circuitry for the operation of the implantable medical device and radio frequency circuitry for transmitting and/or receiving radio frequency telemetry signals are disposed, the electric circuitry and the radio frequency circuitry being interconnected, and wherein the electrically conductive housing has at least one slot therein, and a slot feed is operatively interconnected between the radio frequency circuitry and the slot. In this inventive device, the entire electrically conductive housing with the slot can be tailored to operate as an antenna for the radio frequency telemetry signals without any requirement of an insulating separation between the housing wolves.

Preferably, the electronic circuitry, the radio frequency circuitry, and the interconnection therebetween are enclosed by the electrically conductive housing, so that the housing shields the electric circuitry, the radio frequency circuitry, and the interconnection from external radiation in any direction.

If conducting leads, such as those used in a cardiac pacemaker device, i.e. electrode leads, are provided, they can be arranged to extend from the electrically conductive housing close to a voltage node of an electromagnetic field as arises when the electrically conductive housing operates as an antenna for the radio frequency telemetry signals. This results in a minimum interference between the conducting leads and the antenna function.

Three different general principles regarding the shape and location of the slot are described: a slot which is open at one end thereof and which in the antenna literature often is referred to as a notch antenna; a slot which is closed in both ends thereof and which is preferably provided with a backing cavity; and a slot which is closed at both ends thereof and which is formed as a through-opening that proceeds through the entire thickness of the implantable medical device.

Several types of slot feeds are known in the antenna literature and some of them are suitable to be used in the present invention. Depending on the kind of slot a conductor crossing the slot, an inductive coupling loop within the slot, a conductor crossing a portion of the slot and connected capacitively to the opposite edge of the slot, or a feed including a form of coaxial or wire feed-to-waveguide transition can be used. The latter feed preferably is used when the slot is provided with a backing cavity, where the backing cavity operates as a waveguide to feed the slot.

In the description below it is understood that the antenna of the present invention is operable to transmit or receive radio frequency signals. If a term is used herein that suggests one specific signal direction, it will be appreciated that such a situation encompasses that signal direction and/or its reverse.

DESCRIPTION OF THE DRAWINGS

FIGS. 1a and 1b schematically illustrate, in a top view with a top cover removed and in a side view, respectively, an implantable medical device according to a preferred embodiment of the present invention.

FIGS. 2a and 2b schematically illustrate, in a top view with a top cover removed and in a side view, respectively, a further preferred embodiment of the implantable medical device according to the present invention.

FIG. 6 schematically illustrates, in a side view, an alternative embodiment of a slot feeding for use with the implantable medical device of FIG. 5.

FIG. 7 schematically illustrates, in a side view, another alternative embodiment of a slot feeding for use with the implantable medical device of FIG. 5.

FIGS. 8a and 8b schematically illustrate, in a top view with a top cover removed, and in a side view, respectively, a yet further preferred embodiment of the implantable medical device.

DESCRIPTION OF THE PREFERRED EMBODIMENTS

Figure 3A:
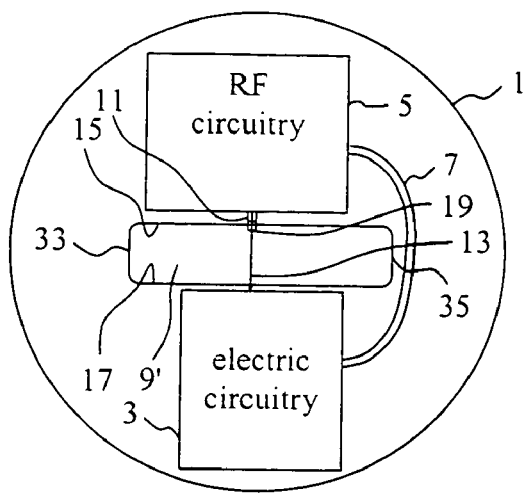
FIGS. 3a and 3b schematically illustrate, in a top view with a top cover removed and in a side view with a slot feeding removed, respectively, a still further preferred embodiment of the implantable medical device.

Throughout the figures similar parts and components, and portions thereof, are denoted by identical reference numerals.

A first preferred embodiment of an implantable medical device of the present invention will be described with reference to FIGS. 1a and 1b. The implantable medical device may be e.g. a pacemaker, an insulin dispenser or other medical equipment including a telemetry link, preferably a high frequency telemetry link.

The implantable medical device has an electrically conductive hollow housing 1, electric circuitry 3 for the operation of the implantable medical device (i.e., for administering a medical therapy), and radio frequency circuitry 5 for transmitting and/or receiving radio telemetry frequency signals. The electric circuitry 3 and the radio frequency circuitry 5 are interconnected (schematically indicated at 7) and are arranged in the electrically conductive housing 1 in a common space or in separate compartments, which may be shielded from each other.

According to the present invention the electrically conductive housing 1 is provided with a slot 9, and feed conductors 11, 13 are interconnected between the radio frequency circuitry 5 and edges 15, 17 of the slot 9. By means of such provisions, the electrically conductive housing can be operated as an antenna for the radio frequency telemetry signals.

In the embodiment of FIGS. 1a and 1b, the slot 9 is open at one end thereof to form a type of antenna usually referred to as a shunt or notch antenna in the antenna literature, see e.g. R. C. Johnson, Antenna Engineering Handbook, third edition, McGraw-Hill, 1993, pages 37-14–37-17, the content of which is incorporated herein by reference. This kind of antenna has been used extensively on aircraft. The length of the slot should be nominally $\lambda/4$ to obtain resonance, where l is the effective wavelength in the dielectric material in the slot 9. The length can be different if tuning components are included.

In FIGS. 1a and 1b the slot 9 is open, and thus blood and surrounding tissue may fill the slot 9. The dielectric constant of such matter may vary considerably, which naturally affect the resonant frequency or wavelength of the antenna. The dielectric material is not important for the radiation performance as such, but tunes the resonance to a lower frequency than that indicated by the physical length of the slot 9. At 400 MHz and a dielectric constant of 1, a quarter of an effective wavelength to obtain resonance measures 18 cm, whereas at a dielectric constant of 65 the resonant slot length is 2.3 cm. Correspondingly, at 2.4 GHz a dielectric constant of 1 gives a resonant l $\lambda/4$ length of 3.1 cm, whereas a dielectric constant of 65 gives a resonant $\lambda/4$ length of 0.39 cm. All these slot lengths except the largest are easily feasible to use in a cardiac pacemaker device, which today typically measures about 3–8 cm in diameter. Also, there is a wide possibility to use shorter slots by suitable impedance matching. The use of a $\lambda/4$ slot as illustrated in FIGS. 1a and 1b is preferred, so as to keep the dimensions small, especially when a frequency around 400 MHz is used.

Preferably, the electronic circuitry 3, the radio frequency circuitry 5, and the interconnection 7 are enclosed by the electrically conductive housing 1 so that the electric circuitry 3, the radio frequency circuitry 5, and the interconnection 7 are shielded from external radio frequency radiation in any direction. Hence, the electrically conductive housing 1 operates similarly to a Faraday cage to effectively hinder radio frequency radiation from entering the housing. With respect to the shielding functionality the conductive housing 1 may have openings of a size that depends on the frequency of the radiation that shall be shielded. Since the electrically conductive housing 1 is typically sealed, particularly hermetically sealed, sealed feed-throughs are required.

One of the feed conductors 13 is therefore provided with a hermetic feed-through 19 in the electrically conductive housing 1 so that the feed conductor 13 can protrude from one of the edges 15 of the electrically conductive housing 1, and extend across the slot 9 to be connected at the opposite edge 17 of the slot 9 to create an electric field within the slot 9 by flowing a feeding current in the feed conductor 13.

Preferably, the feed conductors are a center conductor 13 and a shield conductor 11 of a coaxial cable, with the center conductor 13 being connected at the opposite edge 17 of the slot 9. The conductor 13 may be thicker than an ordinary center conductor of a coaxial cable in the slot 9.

The feed of the antenna may be implemented in any manner known in the art, e.g. by balanced feed or unbalanced feed, and using any kind of antenna tuning circuit or impedance matching network (not illustrated), which loads the antenna with a variable amount of inductance or capacitance to thereby adjust the effective electrical length of the antenna and match the antenna impedance to the impedance of the transmitter/receiver. In this manner, the reactance of the antenna may be tuned out so that the antenna forms a resonant structure at the specified carrier frequency and efficiently transmits/receives far-field radio frequency radiation. Further, radiation-affecting components may be arranged across the slot 9. Capacitors, inductors, or active components may be interconnected between the edges 15, 17 of the slot 9. Capacitances may be implemented as small protrusions at the edges 15, 17 of the slot 9, whereas inductors may be implemented as narrow strips across the slot 9.

The design of the impedance matching network and the slot 9 can be chosen in order to obtain suitable antenna performance in terms of radiation parameters such as resonance frequency, input impedance, bandwidth, radiation pattern, gain, polarization and near-field pattern.

Another way to control the feed impedance is to move the location of the feed conductor 13 along the slot 9.

Preferably, the radiation parameters can be controlled to accommodate for different filling materials in the slot, which have different dielectric properties.

It shall be appreciated that the feed conductor 13 does not necessarily have to cross the slot over its entire width. The feed conductor 13 may for instance make a loop in the slot and be connected to the same slot edge, at which it is fed through the electrically conductive housing 1.

The slot 9 in the embodiment of FIGS. 1a and 1b is located substantially halfway between two opposite edges of the electrically conductive housing, i.e. so that extensions, of the electrically conductive housing 1 on either side of the slot in directions orthogonal to the slot 9, schematically indicated by arrows 21, 23, are of similar sizes. Such a location of the slot 9 allows an optimum antenna performance to be obtained. Locating the slot 9 closer to the circumference of the housing 1 would make the impedance matching more difficult, with the difficulty increasing the closer the slot 9 is to the circumference.

FIGS. 2a and 2b illustrate a second embodiment of the implantable medical device wherein the device is provided with two output conducting leads 25 connected to the electric circuitry 3, where each of the conducting leads 25 is provided with a hermetic feed-through 27. The protrusions of the conducting leads 25 are only schematically indicated in FIGS. 2a and 2b, and it will be appreciated by those skilled in the art that they may be longer. The conducting leads 25 may have different shape and be different in number.

The conducting leads 25 preferably are located where they have as small an influence on the antenna function as possible. This is useful both to avoid influence on the therapy function and to avoid the conducting leads to operate as antennas. In the antenna design procedure an electromagnetic field calculation is typically performed, and one result of such a calculation is the electric field around the implantable medical device, which will give suggestions for suitable locations. In order to thus minimize the interference the conducting leads 25 are located in the slot 9, preferably symmetrically in the slot 9, where the electric field has a minimum. An alternative location is at an opposite edge of the electrically conductive housing 1. The shape of the housing 1 may be less regular than what is illustrated in FIGS. 2a and 2b, but still a position on the circumference of the housing 1 can be found, where a local minimum of the electric field exists.

Further, the slot 9 is filled with a dielectric material 31, particularly a plastic, a glass or a ceramic material. This produces a well-defined dielectric constant of the material 31 in the slot, as well as providing good mechanical support for the conducting leads 25.

A third preferred embodiment of the implantable medical device of the present invention will next be described with reference to FIGS. 3a and 3b. The device has as above, an electrically conductive housing 1, in which electronic circuitry 3, and radio frequency circuitry 5 are interconnected. Feed conductors 11, 13 are interconnected between the radio frequency circuitry 5 and edges 15, 17 of the slot, which in this embodiment has different shape, and is therefore denoted by 9'. The slot 9' is closed at both ends 33, 35 thereof and the antenna thus formed is commonly referred to as a slot or aperture antenna. A slot antenna is an elongated aperture in a conducting surface where one or more feeding elements generate an electric field over the elongated aperture.

The slot 9' has a length preferably that is half an effective wavelength ($\lambda/2$), so as to achieve a resonant structure, but a shorter slot will radiate as well but with gradually more difficult impedance matching problems. A very short slot will also have a narrower instantaneous bandwidth. The shape is not critical for the antenna function and for instance rounded and wider ends, a so-called dumbbell shape, is frequently used to decrease the resonant length.

Below the slot 9' there is provided electric shielding or circuitry (schematically indicated at 40 in FIG. 3b) to prevent the slot from radiating inwardly into the housing 1, which would affect the circuitry therein in an adverse manner. The tissue of the body, which surrounds the implantable medical device, typically has a high electric constant, thereby reducing the length of the $\lambda/2$ slot. This also reduces the amount of radiation directed to the interior of the housing 1.

Figure 3B:
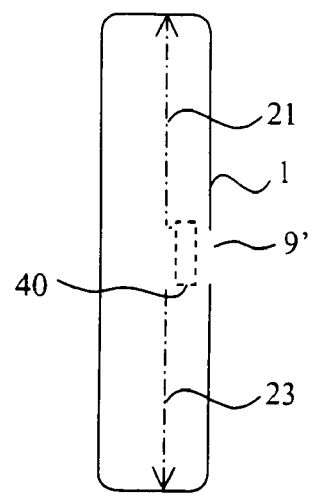

Obviously, there is a natural transition from the $\lambda/2$ slot geometry of FIGS. 3a–b to the $\lambda/4$ notch of FIGS. 1a–b. Provided that the $\lambda/4$ notch is made in a thin structure it can be seen as a $\lambda/2$ slot, which is bent over the edge of the structure.

Figure 4:
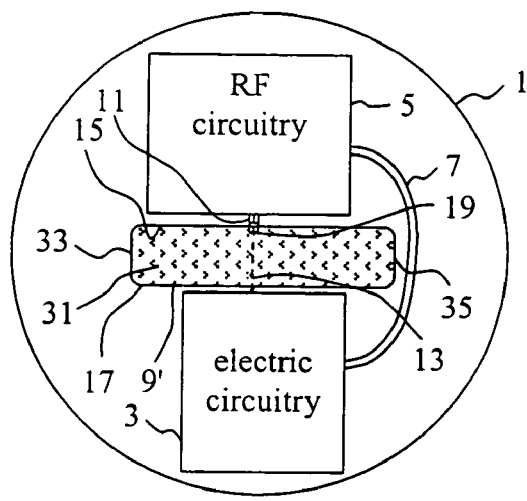
FIG. 4 schematically illustrates, in a top view with a top cover removed, a yet further preferred embodiment of the implantable medical device.

FIG. 4 illustrates a fourth preferred embodiment of the implantable medical device, which is identical with the FIGS. 3a–b embodiment except of that the slot 9' is filled with dielectric material 31 having a known dielectric constant.

Figure 5:
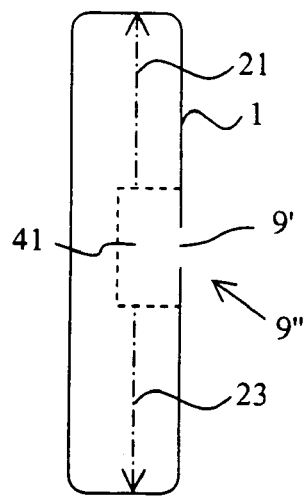
FIG. 5 schematically illustrates, in a side view with a slot feeding removed, a still further preferred embodiment of the implantable medical device.

FIG. 5 illustrates a fifth preferred embodiment of the implantable medical device wherein the slot of a type referred to as a cavity-backed slot 9", and comprises a backing cavity 41 below the slot 9' instead of the shielding 40. In other respects this embodiment is identical with the FIGS. 3a and 3b embodiment.

The backing cavity 41 at the inside of the housing 1 is a rather large structure; it may measure $\lambda/2$ times $\lambda/4$–$\lambda/2$, where $\lambda$ is the effective wavelength in the filling material of the backing cavity 41, if any. The antenna is a cavity resonator fed energized by a feed conductor connected across the slot (not illustrated), which radiates from the slot aperture. Further reference to cavity-backed slot antennas is given in R. C. Johnson, Antenna Engineering Handbook, third edition, McGraw-Hill, 1993, pages 8–7–8–9, the content of which is incorporated herein by reference. Depending on the dielectric constant of the filling material the depth of the cavity 41 will be different, but if the cavity is deeper than the thickness of the implantable medical device, the backing cavity can be turned to be e.g. parallel with the surface of the housing 1, in which the thin slot is made.

In FIG. 6 such a turned cavity 41' for backing of the slot 9' is illustrated. The cavity can be filled with a ceramic material, which is partly metallized and welded or brazed to the electrically conductive housing to form a hermetic sealing. The feed to the slot 9' can include a coaxial feed-to-waveguide transition. The center conductor 13 of the coaxial feed is connected through a hole in the ceramic to an edge of the slot 9', whereas the shield conductor 11 is connected to the metallized ceramic. The ceramic should not be metallized in the slot 9'. The length of the cavity 41' preferably is about a quarter of an effective wavelength to obtain a high impedance at the slot 9'.

In FIG. 7 an alternative feed for the turned cavity-backed slot 9" is shown. A bottom end of the cavity, denoted 41", is provided with a second slot 42. A wire 13', possibly on a printed circuit board 43, below the second slot 42 can be adapted to feed the second slot 42 to obtain a wire feed-to-waveguide transition. If the ceramic has a high dielectric constant the second slot 42 will be too short to radiate toward the electric circuitry in the housing 1. A ground connector 11' or similar of the printed circuit board 43 is conveniently connected to the metallized portion of the ceramic-filled cavity 41".

A sixth preferred embodiment of the implantable medical device will next be described with reference to FIGS. 8a and 8b. The device has as above an electrically conductive housing 1, in which electric circuitry 3, and radio frequency circuitry 5 are interconnected. Feed conductors 11, 13 are interconnected between the radio frequency circuitry 5 and edges 15, 17 of the slot, which in this embodiment is a through opening 9''' through the complete thickness of the housing 1. This eliminates the need for a cavity.

It will be appreciated by those skilled in the art that in an alternative version of this embodiment, the through opening 9''' is filled with dielectric material (not illustrated).

Figure 9:
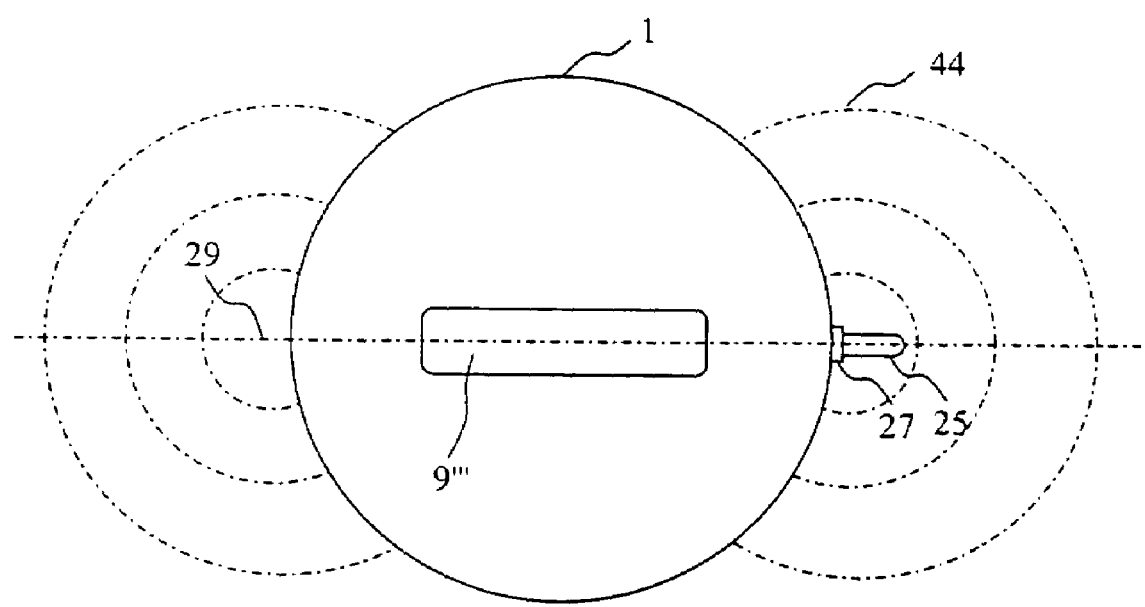
FIG. 9 schematically illustrates, in a top view, a still further preferred embodiment of the implantable medical device.

FIG. 9 illustrates a seventh preferred embodiment of the implantable medical device wherein the device is provided with a conducting lead 25 protruding from the housing 1 via a hermetic feed-through 27. The conducting lead 25 is connected to the electric circuitry of the implantable medical device (not illustrated in FIG. 9 for simplicity). The conducting lead 25 protrudes from the housing 1 at a position along an extension line 29 of the slot 9'''. In other respects this embodiment is identical with the embodiments of FIGS. 8a and 8b.

Generally, the conducting lead 25 protrudes from the housing 1 close to a voltage node of an electromagnetic field, as arises when the electrically conductive housing 1 operates as the antenna for the radio frequency signals. Such a voltage node can be found by calculating or measuring the electric field generated by the implantable medical device. In FIG. 9 equipotential surfaces of the electric field are denoted by 44.

It shall be appreciated that the slots in the embodiments as described above does not have to be formed along a straight line, but may have any suitable elongated shape.

The slot-based antenna as used in the present invention is formed on a metallic structure, the shape of which is determined by special requirements, and which should not be changed by the presence of the slot.

It shall still further be appreciated that the implantable medical device may be provided with two or more slots with separate feeds. Thus, such an implantable medical device may be adapted for transmitting and/or receiving radio frequency waves in at least two different frequency bands, e.g. both around 400 MHz and around 2.4 GHz.

Although modifications and changes may be suggested by those skilled in the art, it is the intention of the inventor to embody within the patent warranted hereon all changes and modifications as reasonably and properly come within the scope of his contribution to the art.

I claim as my invention:

1. An implantable medical device comprising:
   an electrically conductive housing;
   electronic circuitry for producing a medical therapy;
   radio-frequency circuitry for at least one of transmitting radio-frequency signals and receiving radio-frequency signals;
   said electronic circuitry and said radio-frequency circuitry being interconnected by an interconnection, and disposed in said electrically conductive housing;
   said electrically conductive housing having at least one slot therein; and
   a slot feed operatively interconnected between said radio-frequency circuitry and said at least one slot, allowing said electrically conductive housing with said at least one slot to operate as an antenna that detects said radio-frequency signals.

2. An implantable medical device as claimed in claim 1 wherein said electronic circuitry, said radio-frequency circuitry and said interconnection are enclosed by said electrically conductive housing.

3. An implantable medical device as claimed in claim 1 wherein said electrically conductive housing is sealed.

4. An implantable medical device as claimed in claim 3 wherein said slot feed comprises a hermetically sealed feed-through in said electrically conductive housing.

5. An implantable medical device as claimed in claim 4 wherein said slot feed is disposed across said slot.

6. An implantable medical device as claimed in claim 4 wherein said slot feed comprises a center conductor and a shield conductor of a coaxial cable.

7. An implantable medical device as claimed in claim 1 wherein said slot has opposite ends, and is closed at both of said opposite ends.

8. An implantable medical device as claimed in claim 7 wherein said slot has an interior radiation shielding.

9. An implantable medical device as claimed in claim 7 wherein said slot is a cavity-backed slot.

10. An implantable medical device as claimed in claim 7 wherein said slot is a through opening in said electrically conductive housing.

11. An implantable medical device as claimed in claim 1 wherein said slot has opposite ends, and is open at one of said opposite ends.

12. An implantable medical device as claimed in claim 11 comprising at least one electrically conducting lead having a hermetically sealed feed-through connected to said electronic circuitry and disposed in said slot.

13. An implantable medical device as claimed in claim 1 wherein said slot is a cavity-backed slot.

14. An implantable medical device as claimed in claim 13 wherein said slot feed includes a coaxial feed-to-waveguide transition.

15. An implantable medical device as claimed in claim 13 wherein said slot feed includes a wire feed-to-waveguide transition.

16. An implantable medical device as claimed in claim 1 comprising at least one electrically conductive lead connected to a hermetically sealed feed-through, said hermetically sealed feed-through being connected to said electronic circuitry, said lead protruding from said electrically conductive housing at a position along a line extending from said slot.

17. An implantable medical device as claimed in claim 1 comprising at least one electrically conductive lead connected to a hermetically sealed feed-through, said hermetically sealed feed-through being connected to said electronic circuitry, said lead protruding from said electrically conductive housing close to a voltage node of electromagnetic field arising when said electrically conductive housing is operated as said antenna for said radio-frequency signals.

18. An implantable medical device as claimed in claim 1 wherein said slot is disposed with extensions of said electrically conductive housing on opposite sides of said slot, in respective directions orthogonal to said slot, are of substantially equal size.

19. An implantable medical device as claimed in claim 1 comprising dielectric material at least partially filling said slot.

20. An implantable medical device as claimed in claim 19 wherein said dielectric material is a ceramic.

21. An implantable medical device comprising:
an electrically conductive housing;
radio-frequency circuitry for transmitting radio-frequency signals and receiving radio-frequency signals;
said electronic circuitry and said radio-frequency circuitry being interconnected by an interconnection, and disposed in said electrically conductive housing; and
means for forming a loop antenna that includes the electrically conductive housing as an element that detects said radio-frequency signals.

22. An implantable medical device comprising:
a sealed, electrically conductive housing that defines at least one slot therein;
telemetry circuitry that is operative to generate telemetry signals, wherein the telemetry circuitry is disposed in the electrically conductive housing; and
a conductor interconnected in said housing between the telemetry circuitry and the slot, said conductor comprising a coaxial cable having a center conductor and a shield conductor said shield conductor being electrically connected to said housing at said slot.

23. An implantable medical device as claimed in claim 22 wherein the conductor is disposed across the slot.

24. An implantable medical device as claimed in claim 22 wherein the slot has opposite ends, and is closed at both of said opposite ends.

25. An implantable medical device as claimed in claim 22 wherein said slot has an interior radiation shielding.

26. An implantable medical device as claimed in claim 22 wherein said slot is a cavity-backed slot.

27. An implantable medical device as claimed in claim 22 wherein said slot is a through opening in said electrically conductive housing.

28. An implantable medical device as claimed in claim 22 wherein said slot has opposite ends, and is open at one of said opposite ends.

* * * * *